(12) United States Patent
Kartalian et al.

(10) Patent No.: US 9,101,399 B2
(45) Date of Patent: Aug. 11, 2015

(54) ANCHORING SYSTEMS AND METHODS FOR SURGERY

(71) Applicant: ProActive Orthopedics, LLC, Great Falls, VA (US)

(72) Inventors: George Kartalian, Great Falls, VA (US); Jordan Jacobs, Randolph, MA (US)

(73) Assignee: ProActive Orthopedics, LLC, Great Falls, VA (US)

( * ) Notice: Subject to any disclaimer, the term of this patent is extended or adjusted under 35 U.S.C. 154(b) by 26 days.

(21) Appl. No.: 13/732,092

(22) Filed: Dec. 31, 2012

(65) Prior Publication Data

US 2013/0245701 A1    Sep. 19, 2013

Related U.S. Application Data

(60) Provisional application No. 61/581,345, filed on Dec. 29, 2011.

(51) Int. Cl.
*A61B 17/88* (2006.01)
*A61B 17/68* (2006.01)
*A61B 17/04* (2006.01)
(Continued)

(52) U.S. Cl.
CPC ............. *A61B 17/68* (2013.01); *A61B 17/0401* (2013.01); *A61B 17/88* (2013.01); *A61B 17/8085* (2013.01); *A61B 17/842* (2013.01); *A61B 2017/00004* (2013.01); *A61B 2017/00862* (2013.01); *A61B 2017/00893* (2013.01); *A61B 2017/0409* (2013.01)

(58) Field of Classification Search
CPC ..................... A61B 17/842; A61B 2017/1775; A61B 17/88
See application file for complete search history.

(56) References Cited

U.S. PATENT DOCUMENTS 3,312,139 A    4/1967   Di Cristina
3,469,573 A    9/1969   Florio
(Continued)

FOREIGN PATENT DOCUMENTS

RU    2269959 C1    2/2006

OTHER PUBLICATIONS

International Search Report and Written Opinion corresponding to the PCT/US08/71961 application dated Oct. 27, 2008.
(Continued)

*Primary Examiner* — David Bates
*Assistant Examiner* — Samuel Hanna
(74) *Attorney, Agent, or Firm* — Muir Patents, PLLC

(57) ABSTRACT

A surgical ring and related methods for plantar plate reconstruction and other surgical procedures are described. In particular, the described anchoring systems and surgical methods may include an anchor configured to wrap at least partially around a first bone associated with an affected joint, and wrap at least partially around a tissue alongside the first bone. The anchor may be compressed in a number of ways so as to compress the tissue alongside the first bone against the first bone. The anchor may be formed from a compressible material, configured with an open shape, and/or include mechanically closeable or compressible features, and the like. The anchor may be formed from various materials including non-bioabsorbable, bioabsorbable, and/or superelastic materials. The first bone may be a metatarsal or phalanx and the tissue alongside the first bone may be a ligament, a plantar plate, or similar tissue.

21 Claims, 19 Drawing Sheets

(51) Int. Cl.
   *A61B 17/80* (2006.01)
   *A61B 17/84* (2006.01)
   *A61B 17/00* (2006.01)

(56) References Cited

U.S. PATENT DOCUMENTS

| | | | |
|---|---|---|---|
| 4,409,974 A | 10/1983 | Freedland | |
| 4,456,005 A | 6/1984 | Litchy | |
| 4,688,561 A | 8/1987 | Reese | |
| 4,796,612 A | 1/1989 | Reese | |
| 4,858,601 A | 8/1989 | Glisson | |
| 5,061,137 A | 10/1991 | Gourd | |
| 5,102,276 A | 4/1992 | Gourd | |
| 5,167,664 A | 12/1992 | Hodorek | |
| 5,217,462 A | 6/1993 | Asnis | |
| 5,250,049 A | 10/1993 | Michael | |
| 5,529,075 A | 6/1996 | Clark | |
| 5,827,285 A | 10/1998 | Bramlet | |
| 5,908,421 A | 6/1999 | Beger | |
| 5,993,486 A | 11/1999 | Tomatsu | |
| 6,203,545 B1 | 3/2001 | Stoffella | |
| 6,283,973 B1 | 9/2001 | Hubbard et al. | |
| 6,348,053 B1 | 2/2002 | Cachia | |
| 6,458,134 B1 | 10/2002 | Songer et al. | |
| 6,464,706 B1 | 10/2002 | Winters | |
| 6,736,819 B2 | 5/2004 | Tipimeni | |
| 6,887,243 B2 | 5/2005 | Culbert | |
| 6,890,333 B2 | 5/2005 | Von Hoffmann et al. | |
| 6,908,465 B2 | 6/2005 | Von Hoffmann et al. | |
| 6,942,668 B2 | 9/2005 | Padget et al. | |
| 7,008,428 B2 | 3/2006 | Cachia et al. | |
| 7,070,601 B2 | 7/2006 | Culbert et al. | |
| 7,097,647 B2 | 8/2006 | Segler | |
| 7,112,221 B2 | 9/2006 | Harris | |
| 7,175,667 B2 | 2/2007 | Saunders et al. | |
| 7,291,175 B1 | 11/2007 | Gordon | |
| 7,326,211 B2 | 2/2008 | Padget et al. | |
| 7,625,395 B2 | 12/2009 | Muckter | |
| 7,833,227 B2 | 11/2010 | Fernandez | |
| 7,875,058 B2 | 1/2011 | Holmes, Jr. | |
| 7,951,198 B2 | 5/2011 | Sucec et al. | |
| 7,955,388 B2 | 6/2011 | Jensen et al. | |
| 8,221,455 B2 | 7/2012 | Shurnas et al. | |
| 8,277,459 B2 | 10/2012 | Sand et al. | |
| 8,398,678 B2 | 3/2013 | Baker et al. | |
| 8,425,554 B2 | 4/2013 | Denove et al. | |
| 2001/0049529 A1 | 12/2001 | Cachia et al. | |
| 2002/0198527 A1 | 12/2002 | Muckter | |
| 2003/0236555 A1 | 12/2003 | Thornes | |
| 2004/0138665 A1 | 7/2004 | Padget et al. | |
| 2004/0158253 A1 | 8/2004 | Liou | |
| 2004/0199165 A1 | 10/2004 | Culbert et al. | |
| 2004/0260297 A1 | 12/2004 | Padget et al. | |
| 2005/0177167 A1 | 8/2005 | Muckter | |
| 2005/0187555 A1 | 8/2005 | Bideremann et al. | |
| 2005/0240187 A1 | 10/2005 | Huebner et al. | |
| 2005/0281633 A1 | 12/2005 | Mercer | |
| 2006/0235410 A1 | 10/2006 | Ralph et al. | |
| 2006/0271054 A1 | 11/2006 | Sucec et al. | |
| 2006/0271055 A1 | 11/2006 | Thramann | |
| 2006/0276793 A1 | 12/2006 | Berry | |
| 2007/0162124 A1 | 7/2007 | Whittaker | |
| 2008/0172097 A1 | 7/2008 | Lerch et al. | |
| 2008/0177291 A1 | 7/2008 | Jensen et al. | |
| 2008/0208252 A1 | 8/2008 | Holmes | |
| 2009/0036893 A1 | 2/2009 | Kartalian et al. | |
| 2009/0131936 A1 | 5/2009 | Tipimeni et al. | |
| 2009/0210016 A1 | 8/2009 | Champagne | |
| 2009/0228049 A1 | 9/2009 | Park | |
| 2010/0076504 A1 | 3/2010 | McNamara et al. | |
| 2010/0211071 A1* | 8/2010 | Lettmann et al. | 606/60 |
| 2010/0249855 A1 | 9/2010 | Bless | |
| 2011/0077656 A1* | 3/2011 | Sand et al. | 606/96 |
| 2011/0118780 A1 | 5/2011 | Holmes | |
| 2011/0130789 A1 | 6/2011 | Shurnas et al. | |
| 2011/0166574 A1 | 7/2011 | Hsu | |
| 2011/0224738 A1 | 9/2011 | Sucec et al. | |
| 2011/0301648 A1 | 12/2011 | Lofthouse et al. | |
| 2012/0016426 A1 | 1/2012 | Robinson | |
| 2012/0016428 A1 | 1/2012 | White et al. | |
| 2012/0071935 A1 | 3/2012 | Keith et al. | |
| 2012/0101502 A1 | 4/2012 | Kartalian et al. | |
| 2012/0330322 A1 | 12/2012 | Sand et al. | |
| 2013/0030475 A1 | 1/2013 | Weiner et al. | |
| 2013/0030480 A1 | 1/2013 | Donate et al. | |
| 2013/0138150 A1 | 5/2013 | Baker et al. | |
| 2013/0158609 A1 | 6/2013 | Mikhail et al. | |
| 2013/0184708 A1* | 7/2013 | Robinson et al. | 606/60 |
| 2013/0245700 A1 | 9/2013 | Choinski | |
| 2013/0245701 A1 | 9/2013 | Kartalian et al. | |

OTHER PUBLICATIONS

Foot & Ankle International, "The Arthrex, Tight Rope™ Fixation System".2007.

Timothy Charlton, M.D. "ZipTight™ Fixation System, featuring Zip Loop Technology: Ankle Syndesmosis." Surgical Protocol, Biomet Sports Medicine. Mar. 2009.

Coughlin et al. "Proximal metatarsal osteotomy and distal soft tissue reconstruction as treatment for hallux valgus deformity". Keio J Med 2005; 54 (2): 60-65. Apr. 21, 2005.

* cited by examiner

ANCHORING SYSTEMS AND METHODS FOR SURGERY

CROSS-REFERENCE TO RELATED APPLICATIONS

This U.S. non-provisional patent application claims priority under 35 U.S.C. §119(e) to U.S. provisional application Ser. No. 61/581,345, filed Dec. 29, 2011, the entire contents of which are hereby incorporated by reference.

BACKGROUND OF THE INVENTION

1. Field of the Invention

Anchoring systems and methods are disclosed that may have multiple uses in orthopaedic surgery such as joint reconstruction, ligament reconstruction, plantar plate stabilization, and similar procedures. More particularly, the anchoring system may include systems and methods for anchoring tissue, such as a plantar plate and the like, to an associated bone during and after reconstructive surgery.

2. Related Art

Various devices and methods have been used in the prior art for bone realignment, fixation of the bones or bone portions, and ligament reconstruction repair in order to correct for various orthopaedic conditions, such as hallux valgus, tarsometatarsal sprains, ankle ligament reconstruction, and spring ligament repair. In various reconstructive surgeries, there may be disruption of tissue associated with a bone, or joint, that is difficult to correct based on a number of factors, including, for example, access to the tissue and/or joint, and/or various stressors that arise from realignment of bones, ligaments, etc. due to the surgery. One example of such complications involves a reconstruction of the lesser toe joints. On the bottom of each lesser toe joint there is a ligament between the base of the toe and the metatarsal behind the joint, known as the plantar plate. The plantar plate acts to keep the toe in the joint and to keep the toe from elevating out of the joint. Due to various stresses, including e.g. acute injury and extended wear, the plantar plate can become overstretched or tear causing pain, deformity, and/or dislocation of the toe. The plantar plate may be partially or completely detached from the bone, requiring reattachment. In certain situations, one or more toes may need to be realigned into the joint and stabilized. This may involve the plantar plate being tightened and/or surgically repaired. Such procedures may be similar to, and/or included as part of, a correction of hammer toe deformity, hallux valgus (bunion) and the like. Repair of the plantar plate may involve re-anchoring the ligament to the associated metatarsal and/or proximal phalanx. According to known methods this may involve pinning the ligament to the associated bone to hold the structures together during healing, and typically includes the use of external restraining devices, such as a boot, for an extended period during healing.

There are numerous types of surgical procedures that may be employed to correct joint deformities, such as a bunion, that may also disrupt, and/or cause additional stress to, associated ligaments. For example, various osteotomies to realign the first metatarsal (MT) and the first metatarsophalangeal (MTP) joint do not function through the axis of deformity. Rather, they attempt to realign the bone and joint by translating and rotating the MT through a location that is accessible and minimizes complications. However, there are several complications related to altering mechanical and biological physiology of the MT, such as altering the length and position of the MT associated with this surgical procedure. Furthermore, the trauma to and shortening of the bone from sawing, and the overall disruption and weakening of attachments during what can be a prolonged healing time, may all lead to less than satisfactory results, such as re-injury of the affected joint, and/or inadequate healing. For example, as a result of corrective and reconstructive surgeries involving the metatarsal joints, the plantar plate may be disrupted during, or after, the surgery resulting in e.g. lateral or dorsal displacement of the plantar plate.

Various known corrective surgeries, such as those described above, have numerous disadvantages and drawbacks including disruption of tissues associate with the joint. Accordingly, there is an ongoing need for improved systems and methods that address current limitations in securing tissue to associated bones, including improving the strength, endurance and ease of securing ligaments of the affected joint to bones and the like.

SUMMARY

Anchoring systems and surgical methods are disclosed that may optimize the surgical reconstruction of joints, bones and/or associated tissue. Systems and methods disclosed herein may allow for reconstruction of bone(s) and/or associated tissue, such as that of a joint. Some examples relate to plantar plate (PP) reconstruction that from a biomechanical and biological standpoint that may be advantageous over conventional devices and techniques currently used for joint stabilization, bunion correction and/or ligament reconstruction surgery or similar procedures.

Aspects of the invention may find applicability, for example, in combined dorsal and plantar surgical approaches for implantation at the MTP joint, soft tissue release performed dorsally along with a proximal interphalangeal (PIP) joint arthroplasty done more distally, e.g. if a rigid hammertoe is part of the deformity, and/or reducing the MTP joint with an attempt to realign and re-secure the native PP, interosseous tendons, and intermetatarsal ligament. However, the invention is not limited thereto, and may be implemented in a number of ways.

According to first aspects, a surgical anchor system for use in the repair of an orthopaedic condition may include an anchor configured to engage a first bone by wrapping, at least partially, around the first bone and a tissue alongside the first bone. In some embodiments, the anchor may have a first state characterized by an open shape, and a second state characterized by a substantially closed ring shape. The anchor may be formed of a deformable material capable of being configured in the first and second shapes.

In some embodiments, the anchor may be non-bioabsorbable and may be fabricated from a material selected from the group consisting of stainless steel and titanium.

In some embodiments, the anchor may have a first closed state in which the anchor may be placed around the first bone and the tissue alongside the first bone, and may be compressible to a second state, in which the anchor compresses the tissue along side the first bone against the first bone.

In some embodiments, the anchor may include a superelastic material, such as nitonol. In embodiments, the anchor may include a bioabsorbable material, and/or may be fabricated from a material selected from the group consisting of polylactic acid, bone allograft, and hydroxyapatite coral. In embodiments, the anchor may be osteogenic and coated with a bone growth factor.

In some embodiments, the anchor may include attachment points configured to secure at least one of the first bone and the tissue to the anchor.

In some embodiments, the anchor may be a primary anchor, and a secondary anchor may be configured to engage a second bone and to connect to the primary anchor.

In some embodiments, the secondary anchor may be configured to connect to the primary anchor via a connector component including an engagement mechanism. In embodiments, the engagement mechanism may include a mating engagement between an interior surface of at least one of the primary anchor and the secondary anchor and the connector component. In embodiments, the engagement mechanism may include a threaded engagement between an interior surface of at least one of the primary anchor and the secondary anchor and the connector component.

In some embodiments, a secondary anchor may be configured to be inserted, at least partially, into a second bone.

In some embodiments, the first bone and/or the second bone may be a metatarsal. In embodiments, the tissue alongside the first bone may be a plantar plate.

In some embodiments, a connector component may be fabricated from a material selected from the group consisting human dermis, porcine intestinal mucosa, porcine intestinal mucosa, fetal bovine skin, porcine skin, cadeveric fascia, polytetrafluoroethylene, polypropylene, marlex mesh, absorbable suture, non-absorable suture, and umbilical tape.

In some embodiments, a secondary anchor may be further configured to wrap at least partially around a second bone and a tissue alongside the second bone.

In some embodiments, either, or both, of the primary anchor and the secondary anchor may be adapted to engage the first metatarsal and/or the second metatarsal by wrapping, at least partially, around the metatarsal. In embodiments, either, or both, of the primary anchor and the secondary anchor may be contoured to an anatomical shape of a bone to be treated, such as the first or second metatarsal, a phalanx, etc. Such contours may include, for example, developable and/or non-developable surfaces. As used herein, developable surfaces are those with zero Gaussian curvature, e.g. generalized cylinders, cones, etc., whereas non-developable surfaces include Gaussian curvature, e.g. partial spheroids, three-dimensional saddles, depressions, etc. In embodiments, a preformed contour of at least one of the primary anchor and the secondary anchor may include a saddle, or depression, that substantially matches an anatomical shape of the first or second metatarsal.

In some embodiments, either, or both, of the primary anchor and the secondary anchor may include a base, configured to extend axially along a length of a bone to be treated, and one or more flanges attached to the base and extending generally transversely to the base. In embodiments, the base may be configured to extend axially along a length of a metatarsal and the flanges may include a dorsal portion, and/or a plantar portion, configured to wrap over, or under, the metatarsal, respectively.

In some embodiments, either, or both, of the primary anchor and the secondary anchor may be adapted to be secured to a plurality of connectors, e.g. secured to two connectors disposed diagonally, crossing or parallel to one another. In some embodiments, either, or both, of the primary anchor and the secondary anchor may include a plurality of perforations for receiving the connector(s). In embodiments, one or more perforations of the primary or secondary anchor may be threaded for fixedly, or adjustably, securing the connector(s) to the primary or secondary anchor.

In some embodiments, an anchor further may include a separate interior contour configured for holding the tissue alongside the bone.

According to further aspects, a surgical method for repairing and/or reconstructing a joint, may include one or more steps of entering the tissues of the joint by performing at least one incision; placing a first surgical anchor at least partially around a first bone associated with the joint and at least partially around a tissue alongside the first bone; compressing the tissue alongside the first bone against the first bone via the first surgical anchor; and/or closing the incision.

In some embodiments the first bone may be one of a metatarsal and a proximal phalanx and the tissue alongside the first bone may include a plantar plate.

Embodiments may include securing a second surgical anchor to a second bone; and securing the first surgical anchor to the second surgical anchor.

In some embodiments, the second bone may be at least one of a metatarsal and a proximal phalanx.

Embodiments may include compressing the primary anchor around the first bone and the tissue alongside the first bone.

Embodiments may include closing the primary anchor from a first state, in which the primary anchor is in an open shape, to a second state, in which the primary anchor is in a substantially closed ring shape.

Embodiments may include compressing the primary anchor from a first closed state, in which the primary anchor has a first inner circumference, to a second closed state, in which the primary anchor has a second inner circumference that is smaller than the first inner circumference.

Embodiments may include one or more steps of creating a bore across a second bone; inserting a connector component through the bore; securing the connector component to an outer surface of the primary anchor; and securing the connector component to the secondary anchor.

Embodiments may include attaching a clip to a portion of the connector component that substantially prevents the connector component from pulling back through the primary anchor.

Embodiments may include adjustably engaging a portion of the connector component with an interior surface of the secondary anchor.

Embodiments may include adjustably engaging a threaded portion of the connector component with a threaded interior surface of the secondary anchor.

Embodiments may include compressing a tissue alongside the second bone to the second bone.

Embodiments may include placing separate surgical anchors around each of at least two respective metatarsals or phalanges and at least partially around a tissue lying alongside each of the respective metatarsals or phalanges; and compressing the tissue lying alongside each of the respective metatarsals or phalanges to the respective metatarsals or phalanges via the separate surgical anchors.

Embodiments may include one or more steps of penetrating the tissue alongside the first bone with an elongated member fed through a positioning device; adjusting a position of the tissue alongside the first bone with the positioning device such that the tissue is at least partially within the first surgical anchor; and/or fixing the tissue to the first surgical anchor with the elongated member.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification; illustrate embodiments of the invention and together with the detailed description serve to explain the principles of the invention. No attempt is made to show structural details of the invention in more detail than may be necessary for a fundamental understanding of the invention and various ways in which it may be practiced.

DETAILED DESCRIPTION OF THE INVENTION

Figure 1A:
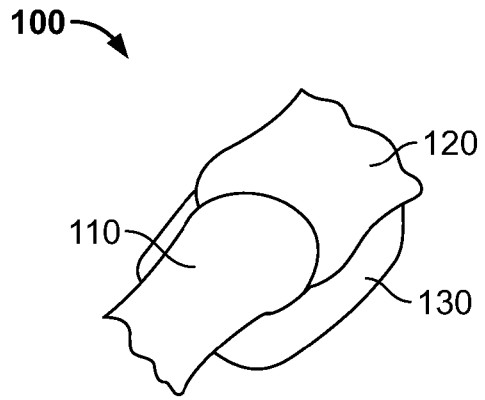
FIGS. 1A-1C are isometric and axial views of an exemplary joint structure.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is to be noted that as used herein and in the appended claims, the singular forms "a," "an," and "the" include the plural reference unless the context clearly dictates otherwise. This, for example, a reference to "an anchor" is a reference to one or more anchors and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Moreover, provided immediately below is a "Definition" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

BMP is bone morphogenetic protein.
bFGF is basic fibroblast growth factor.
GAMs are gene-activated matrices.
IM is the intermetatarsal angle.
HV is the hallux valgus angle.
MT is metatarsal.
MTP joint is metatarsophalangeal joint.
PLA is polylactic acid.

The term "intermetatarsal angle" or "IM angle," as used herein generally refers to the angle that may be measured between the line of the first and second metatarsal shafts. In the normal foot, the IM angle is in the range of about 6 degrees to about 9 degrees. In a patient afflicted with hallux valgus, the IM angle is about 15 degrees.

The term "hallux valgus angle" or "HV angle," as used herein generally refers to the angle that may be measured between the line of the first metatarsal shaft and the proximal phalanx. In the normal foot, the HV angle is in the range of about 9 degrees to about 10 degrees. In a patient afflicted with hallux valgus, the HV angle is about 30 degrees.

The terms "active agent," "drug," "therapeutic agent," and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned that also induce the desired pharmacologic effect. In particular, the therapeutic agent may encompass a single biological or abiological chemical compound, or a combination of biological and abiological compounds that may be required to cause a desirable therapeutic effect.

By the terms "effective amount" or "therapeutically effective amount" of an agent as provided herein are meant a nontoxic but sufficient amount of the agent to provide the desired therapeutic effect. The exact amount required will vary from subject to subject, depending on the age, weight, and general condition of the subject, the severity of the condition being treated, the judgment of the clinician, and the like. Thus, it is not possible to specify an exact "effective amount." However, an appropriate "effective" amount in any individual case may be determined by one of ordinary skill in the art using only routine experimentation.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, the present method of "treating" individuals afflicted with hallux valgus, as the term "treating" is used herein, encompasses treatment of hallux valgus in a clinically symptomatic individual.

The terms "condition," "disease" and "disorder" are used interchangeably herein as referring to a physiological state that can be detected, prevented or treated by the surgical techniques, devices and/or therapeutic agent as described herein. Exemplary diseases and conditions in which the anchoring system, methods, and therapeutic agents of the invention may be used may include, but are not limited to claw toes, hammertoe, hallux valgus, plantar plate disruption, metarsalgia, pre-dislocation syndrome, cross-over toe deformity, and instability of the metatarsophalangeal joint, or similar conditions of the foot, hand, and other joints.

The term "patient" as in treatment of "a patient" refers to a mammalian individual afflicted with or prone to a condition, disease or disorder as specified herein, and includes both humans and animals.

The term "biomaterial," as used herein generally refers any suitable natural, synthetic material, absorbable, non-absorbable, or recombinant material such as extracellular matrix bioscaffolds, cadaveric fascia, suture-type materials, or umbilical tape that may be used as part of the anchoring system of the invention. As the skilled artisan will appreciate, biomaterial may be may be flexible and/or elastic, or more rigid, dependent on usage. The biomaterial may have a structure of a string, cord and/or strap in some embodiments.

The term "bioabsorbable" as used herein generally may include a bioabsorbale material such as poly-D, L-lactic acid, polyethylene glycol, polydioxanone, polylactic acid, 70L/30DL polylactide, polyglycolide, poly(orthoester), calcium sodium metaphosphate, hydroxyapatite, calcium phosphate, polytetra fluoroethylene, collagen I, II, IX, X, and XI, durapatite, and hydrogel.

The terms "polymer" or "biopolymer," as used herein generally refer to a compound having two or more monomer units, and is intended to include linear and branched polymers, and copolymers, the term "branched polymers" encompassing simple branched structures as well as hyperbranched and dendritic polymers. The term "monomer" is used herein to refer to compounds that are not polymeric. "Polymers" or "biopolymers" herein may be naturally occurring, chemically modified, or chemically synthesized.

The term "cortex" as used herein, generally refers the outer wall of a bone.

The disclosed surgical anchoring system may have multiple uses in orthropaedic surgery. In particular, surgical anchoring system may be used in surgical procedures for reconstructing and/or repairing joints, including joint stabilization and/or reconstruction pursuant to other procedure, such as plantar plate reconstruction, osteotomies, etc. The disclosed surgical anchoring system may include a system for securing and/or compressing a bone and tissue lying alongside the bone, such as ligaments, tendons, and the like.

According to aspects, improvements in stabilizing a joint, such as joint 100 depicted in FIG. 1A, may be achieved. In exemplary embodiments, a joint 100 may include a first bone 110, such as a metatarsal, and another bone 120, such as a proximal phalanx. Tissue 130 associated with the joint, such as a plantar plate, may be naturally connected with first bone 110 and/or other bone 120. As a result of various injuries, impairment and/or surgical procedures, however, a pre-existing connection of the tissue 130 may be disturbed, which includes being impaired, damaged, or completely disconnected, with respect to the first bone 110 and/or other bone 120.

Figure 1B:
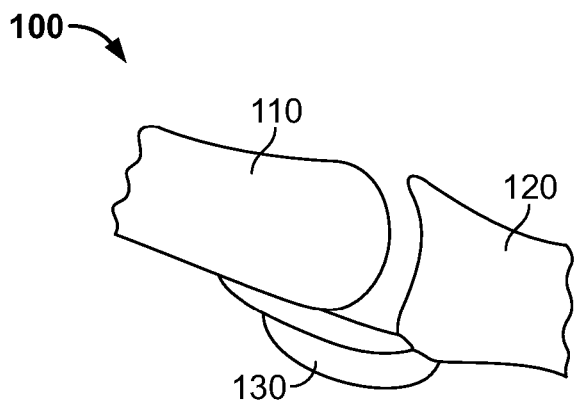
Figure 1C:
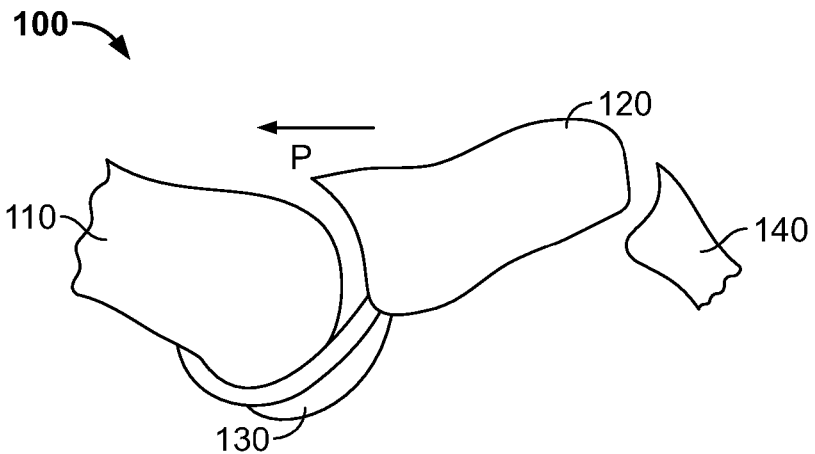

Further details regarding exemplary joint 100 are shown in the axial views depicted in FIGS. 1B and 1C and described with respect to a MTA joint. As shown in FIG. 1B, the metatarsal 110 may normally be naturally connected on an underside of the bone to the proximal phalanx 120 by plantar plate 130. In normal use, the plantar plate 130 provides stabilization to the MTA joint and also cushions impact associated with walking a running. As can be seen in FIG. 1B, the proximal phalanx 120 may normally rotate in a limited range axially about the head of metatarsal 110, limited by for example the flexibility of the plantar plate 130 and the connection of the plantar plate 130 to the metatarsal 110 and proximal phalanx 120. Through traumatic injury, wear, anatomical defects etc., the plantar plate 130 may be disturbed resulting, for example, in conditions such as depicted in FIG. 1C, described below.

As shown in FIG. 1C, a disturbance of the plantar plate 130, such as damage resulting in an elongation of the tissue, and/or a partial or complete disconnection from the metatarsal 110 and/or proximal phalanx 120, may result in a deformity of the MTA joint in which the proximal phalanx 120 is pulled out of alignment by other tissue (not shown) in direction P. Further complications with respect to distal phalanx 140 typically result from such disturbance, such as the distal phalanx assuming a downward angle as shown. In such situations, reattachment and/or reconstruction of the plantar plate 130 may be necessary to correct the stability and/or proper alignment of the bones associated with the joint.

Figure 2:
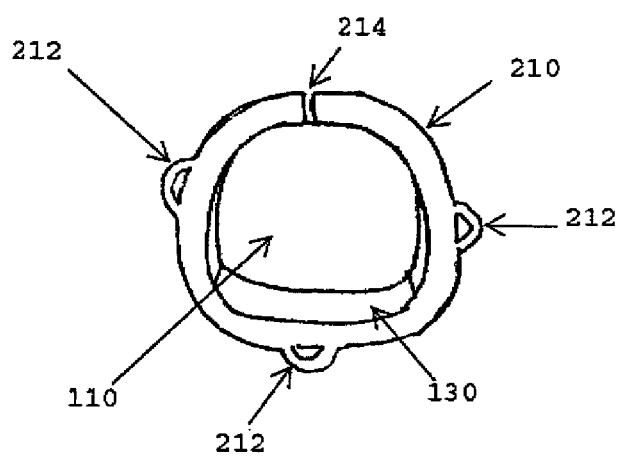
FIG. 2 is a schematic drawing illustrating one embodiment of an anchoring system.

An exemplary surgical reconstruction ring of an anchoring system constructed according to aspects of the invention, such as a primary anchor 210, is depicted in FIG. 2. As shown in FIG. 2, a primary anchor 210 may include connection points such as suture rings 212, and/or a compression opening 214. The primary anchor 210 may be placed at least partially around first bone 110 and a tissue 130 alongside the first bone 110, such as a plantar plate. Thus, in embodiments, a pressure may be applied to the tissue 130 to keep the tissue 130 in contact with the first bone 110, which may advantageously promote re-attachment of a pre-existing connection. To enhance soft tissue to bone healing, the surface of the bone may be roughened or decorticated. Additional sutures, and/or treatments of the first bone 110 and the tissue 130, may be applied, for example, to improve a retaining strength of the tissue 130 to the first bone 110, promote healing, connection, and the like. For example, in embodiments, the primary anchor 210 may be secured at several points mimicking pre-existing tissue connections, such as, for example, with a native PP, e.g. at the plantar proximal phalanx, the medial and lateral collateral ligaments, the intermetatarsal ligament, and/or the plantar metatarsal head. This may include suturing around or through the tissue and/or around an exposed end of bone 110, such as at the metatarsal head, or using a small staple or screw-in device (not shown), to secure the primary anchor 210 to the tissue 130 and/or the bone 110.

Figure 3:
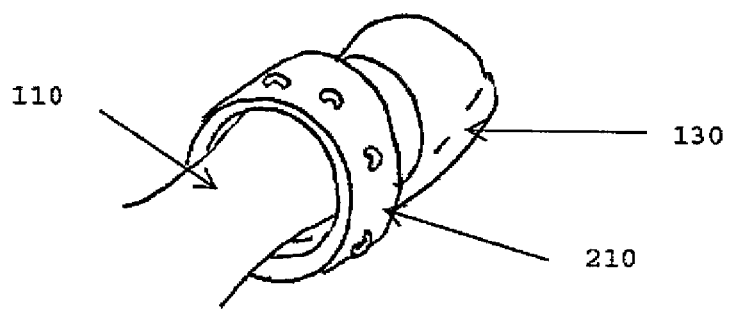
FIG. 3 is an isometric view of the anchoring system and associated physiology as shown in FIGS. 1 and 2.

FIG. 3 depicts an isometric view of the primary anchor 210 positioned with respect to a first bone 110 and tissue 130. In FIG. 3, other bone 120 is not shown. According to embodiments, a first bone 110, such as a metatarsal, may be separated from an associated bone 120 in joint 100 as part a surgical procedure to expose a head and neck region of the bone 110, such as for an osteotomy, and the like. In such embodiments, a surgical ring 210 may be fitted over the exposed head of the first bone 110, such as a metatarsal, and tissue 130, such as a plantar plate.

Figure 4A:
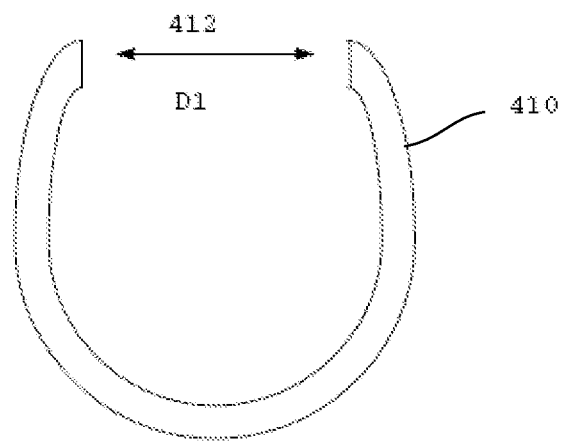
FIGS. 4A and 4B are simplified schematic drawings showing aspects of first and second states of one embodiment of a surgical anchor.
Figure 4B:
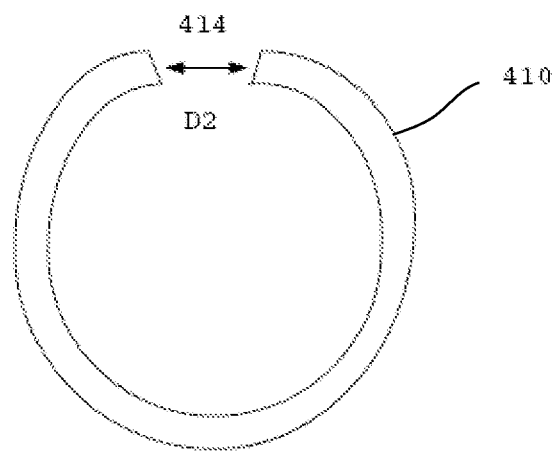

Further aspects of an exemplary surgical anchor 410 are shown with respect to FIGS. 4A and 4B. As shown in FIG. 4A, anchor 410 may be configured in a first state in which the anchor 410 is in an open shape, which may allow for positioning of the anchor with respect to, or around, a bone. An opening 412 in the anchor 410 may have a distance D1. The opening 412 may be configured to provide a desired clearance when applying the anchor 410 to a particular bone.

As shown in FIG. 4B, the anchor 410 may be reconfigured to a second state in which the opening 414 has a distance D2 that is smaller than D1, forming a substantially closed ring shape. As used herein, "substantially closed" should be understood as providing a sufficient encirclement of a bone and associated tissue to prevent the anchor 410 from becoming dislodged from the bone for its intended purpose.

Figure 5A:
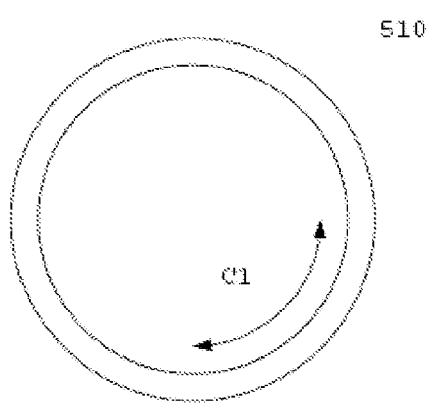
FIGS. 5A and 5B are simplified schematic drawings showing first and second states of another embodiment of a surgical anchor.
Figure 5B:
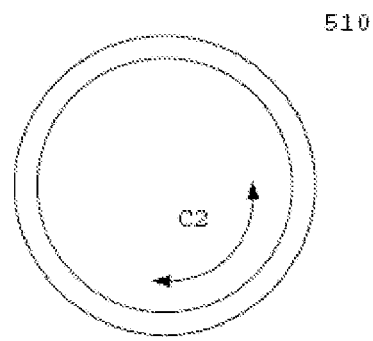

An alternative configuration of an exemplary anchor 510 is shown with respect to FIGS. 5A and 5B. As shown in FIG. 5A, exemplary anchor 510 may be configured in a closed ring shape with an inner circumference C1. Anchor 510 may be formed of a particular material, and/or otherwise configured, to be compressible to second state depicted in FIG. 5B with an inner circumference C2 that is smaller than inner circumference C1 in FIG. 5A. For example, anchor 510, and other anchors and associated components described herein, may be formed, at least partially, from a superelastic material, such as nitonol, and other materials known to those of skill in the art. Such materials may allow for compression of the anchor 510, and the like, around a bone and associated tissue, and for the anchor to substantially maintain a smaller shape after compression. As known by those of skill in the art, the shapes of devices made with compounds such as shape memory alloys, e.g. nitonol, or shape memory polymers, may be contracted without mechanical compression due to, for example, solid state phase transformation.

Alternatively, anchor 510, and other anchors and associated components described herein, may be formed at least partially from a material, or configured in a way, that allows for mechanical compression (or re-compression after an expanding force is released) of the anchor 510 around the bone and associated tissue, e.g. elastic deformation, constricting coils, weaves, etc. Embodiments may include several different ways of securing an incomplete or opened ring around the bone. The material of the ring may be pliable enough to close, and/or to take on a shape that closely approximates the bone, and then be locked in various ways, e.g. suture, wire, or other locking mechanism. Additionally, depending on, for example, whether the material is relatively rigid or flexible, it may be preferable to configure the ring to remain incomplete, i.e. to maintain a gap in the ring, or to have the ends meet to form a complete ring.

In alternative embodiments, the anchor 510, and other anchors and associated components described herein such as anchors 210 and 410, may include, or consist of, bioabsorbable material(s) and may be fabricated from a material selected from the group consisting of polylactic acid, bone allograft, and hydroxyapatite coral. In embodiments, the primary anchor may be osteogenic and coated with a bone growth factor. Such configurations may allow, for example, complete, or partial, absorption of anchors, and/or associated components, described herein. Anchor and/or ring materials may also include demineralized bone material or other osteogenic material (synthetic or natural), which may be absorbable or non-absorbable, flexible or rigid.

Figure 6:
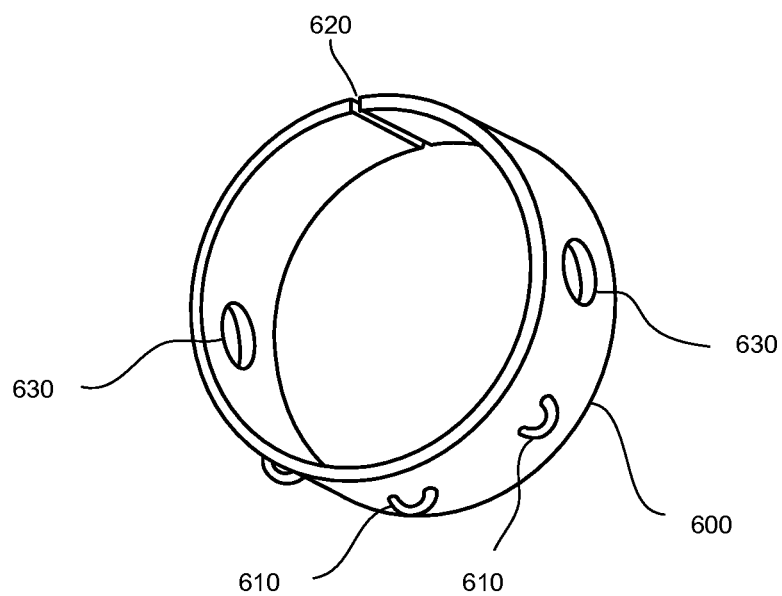
FIG. 6 is an isometric view showing further details of a ring-shaped anchor similar to that shown in FIG. 2.

Additional features are shown with respect to exemplary ring-shaped anchor 600 in FIG. 6. As shown in FIG. 6, an anchor, such as anchor 600, may include one or more attachment points such as suture rings 610, a compression opening 620, and/or through-holes 630. Suture rings 610 may be used, for example, to provide additional connections and attachment strength between the anchor 600 and the tissue associated with the joint, and/or the associated bone, through the use of sutures, and the like.

Compression opening 620 may be used to allow for easy expansion and fitting of the anchor 600 around the bone, and/or to allow for further compression of the anchor 600 around the bone and associated tissue. In embodiments, the anchor 600 may be made from a deformable material that can be closed around the bone, and/or the anchor 600 may include a hinge (not shown) to assist in placement around a bone. In embodiments, the compression opening 620 may be relatively larger than shown in FIG. 6, and, thus, anchor 600 may wrap partially around the bone and tissue. The anchor 600 may be non-bioabsorbable and fabricated from materials such as, for example, plastics, stainless steels, titanium and other alloys. In alternative embodiments, the anchor 600, or portions thereof, may include, or consist of, bioabsorbable material(s) and may be fabricated from, for example, a material selected from the group consisting of polylactic acid, bone allograft, and hydroxyapatite coral. In embodiments, the anchor 600 may be osteogenic and coated with a bone growth factor.

Through-holes 630 may be placed in various locations and used, for example, to provide access to the bone and/or the associated tissue, to place and/or guide attachment screws, and/or allow for a through-bone connector to penetrate the anchor 600 and be secured on either exterior side of the anchor 600. In embodiments, a through-hole 630 may be used to secure a connector component without the connector passing through the bone. For example, a through-hole 630 may have a threaded portion, and the like, for securing to an end of a connector component, thereby securing the bone and the connector component via the anchor 600. In embodiments, one or more through-holes 630 may be threaded, or otherwise adapted, to provide positive engagement with securing screws, attachment bolts and the like.

Figure 7:
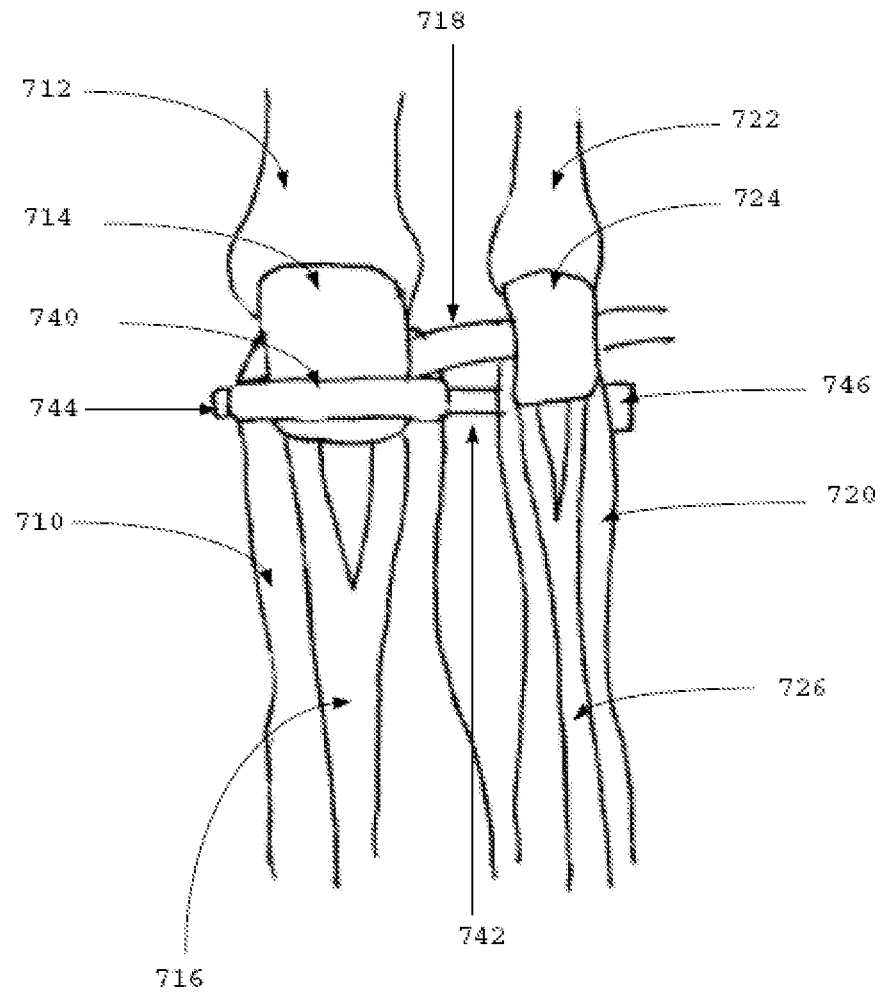
FIG. 7 is a schematic drawing showing a final configuration of an exemplary surgical anchoring system employed for surgical correction of the first MTP joint.

FIG. 7 shows a final configuration of an exemplary surgical anchoring system employed for surgical correction of the first MTP joint. As shown in FIG. 7, a first bone, such as first metatarsal 710, may be connected with the first proximal phalanx 712 by associated tissue, e.g. the lumbrical and interosseous tendons (not shown), and first plantar plate 714 at the MTP joint. A second metatarsal 720 may be connected to the second proximal phalanx 722 by associated tissue, e.g. the lumbrical and interosseous tendons (not shown), and second plantar plate 724 at the adjacent second MTP joint. Processes 716 and 726 of the plantar fascia may further naturally interconnect the plantar plate 714, 724, including natural connection by deep transverse metatarsal ligament (DTML) 718. In various injuries, and/or reconstructive surgeries involving the MTP joint, including osteotomies, realignments, and the like, an attachment of the first plantar plate 714 to the first proximal phalanx 712 and/or the first metatarsal 710 may be disrupted. According to embodiments, a primary anchor 740 may be placed, e.g. wrapped, around an affected bone, such as the first metatarsal 710, and the associated plantar plate, e.g. first plantar plate 714. In the embodiment shown in FIG. 7, the primary anchor 740 is depicted as proximal to the DTML 718, however, alternative positionings are also contemplated. In embodiments, a primary anchor 740 may be connected with a secondary anchor 746 via a connector 742. Connector 742 may be, for example, an adjustable, or fixed length, connector as described further herein. Secondary anchor 746 may be, for example, a through-bone anchor penetrating the second metatarsal 720. Connector 742 may also penetrate the primary anchor 740 and first metatarsal 710 and may be secured to an outer portion of the primary anchor 740 via fastener 744, e.g. pinned, clipped, screwed, etc. Alternatively, connector 742 may be attached to an outer portion of a primary anchor 740, such as by pinning, clipping, screwing, and the like, without penetrating the first metatarsal 710.

In embodiments, the connector component 742 and secondary anchor 746 may provide for precise relative positioning and locking of the secondary anchor in a number of positions along the axial length of the connector component via a one-way ratcheting locking mechanism, a threaded engagement mechanism, and the like. Examples of such connections are described in U.S. Patent Application Publication No. 2009/0036893, which is hereby incorporated by reference. For example, the outer surface of connector component 742 may have a plurality of spaced protrusions such as angular teeth, ridges, barbs, detents, ribs, threads, or the like, which are adapted to be retained in a mating surface provided on the inside surface of the secondary anchor 746. The mating connectors may function to resist motion of the connector component 742 in at least one direction. The locking action formed by the mating connection may act, for example, as a one-way ratcheting mechanism. The mating connections may be forward facing to facilitate motion of the connector component 742 in one direction while resisting movement of the connector component 742 in an opposite direction. Thus, connector component 742 may have fixed stops precut into the connector component for the secondary anchor 746 to lock against. The ratcheting mechanism may thus function similar to a "cable tie," where a locking component slides over the connector component, adjusting its finished length. In addition, the arrangement of the mating connections may be reversed so the projections may be disposed on the inner surface of the secondary anchor and matingly received in the connector component. Other oneway or two-way locking mechanisms may also be employed such as Velcro type connections or other suitable fabrics.

The position of the secondary anchor 746 may be adjusted by pulling on the connector component 742 to move the component relative to anchor 746 and secure it in place via the locking/ratcheting mechanism. This adjustment could also be accomplished by a variety of mechanical means including winding the connector component onto a screw or using a lever for tension. The ratcheting may be automatic or may be actuated by the user. The ratcheting may be permanent or allow for future adjustment. Thus, the locking device may take the form of a releasable, two-way ratcheting device using a mechanism known in the art. Regardless, the invention should not be construed to be limited to any particular locking or ratcheting mechanism, as these types of mechanisms are well known in the art and can be readily made by techniques known to those of ordinary skill in the art.

The connector component 742, and other connectors and associated components described herein, may be composed of suture material that may be elastic, braided, or monofilament in nature, or may be a wire, a polymeric strap, or any other suitable ratcheting material. The connector component 742 may be attached directly to one or both anchors 740, 746 or may be attached by an intermediate mechanism. The connection may be asymmetric to provide greater stiffness or flexibility in one direction over another.

The primary anchor 740 and the secondary anchor 746, and other anchors and associated components described herein, may be composed of a single body and may be wrapped at least partially around, and/or secured into the second metatarsal and first metatarsal, respectively, using such means as screw threads, barbs, loops/cuffs, and the like to result in an interference fit.

The primary anchor 740 and/or the secondary anchor 746, and other anchors and associated components described herein, may be bio-absorbable for short-term use or bioactive for long-term tissue integration and/or may also be coated to reduce the potential for infection or to promote tissue in-growth, as described below.

Alternative placements of the primary anchor 740 are also possible in the context of the MTP joint, such as, positioning the primary anchor 740 distal to the DTML 718, positioning a primary anchor 740 on the first proximal phalanx 712, or similar locations on other metatarsals or phalanges, as well as different bones with respect to joints other than the MTP joint.

Figure 8:
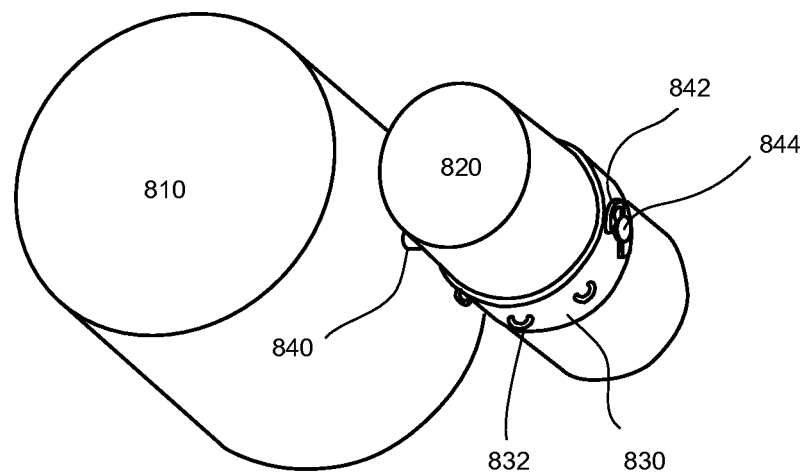
FIG. 8 is a schematic drawing showing one embodiment of the anchoring system of the invention in which the primary anchor includes a ring-shaped anchor disposed around the outside of the bone.

For example, as shown in FIG. 8, a primary anchor 830 may be placed around a second metatarsal 820. Primary anchor 830 may include, for example, suture rings 832, and may be connected with a first metatarsal 810 via a connector 840 secured to an outer portion 842 of the primary anchor 830 by clip 844.

Figure 9:
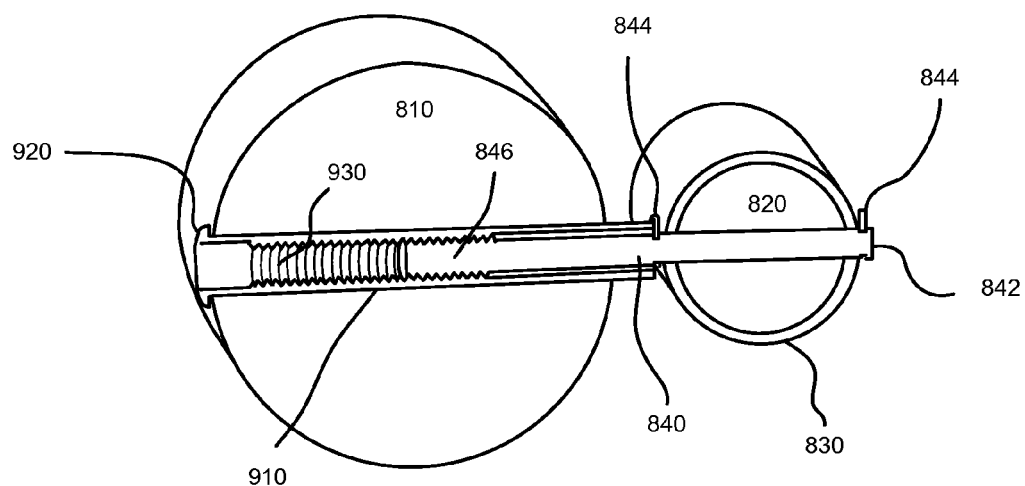
FIG. 9 is a cut-away view showing further details of an exemplary secondary anchor and connector component that may be used with a ring-shaped primary anchor.

Additional details of the exemplary embodiment similar to that depicted in FIG. 8 are shown in FIG. 9. As shown in FIG. 9, primary anchor 830 may wrap around second metatarsal 820, and an associated tissue (not shown). Connector 840 may penetrate both of second metatarsal 820 and first metatarsal 810. A connector end 842 may be secured on an outer surface of the primary anchor 830, for example, by one or more clips 844. A secondary anchor 910 may penetrate the first metatarsal 810 such that an expanded end 920 of the secondary anchor 910 is secured against an outer surface of the first metatarsal 810. Threaded portion 930 of the secondary anchor 910 may be configured to engage with a corresponding threaded portion 846 of connector 840. Thus, a distance between the second metatarsal 820 and first metatarsal 810 may be adjusted. Such configurations may be advantageous, for example, in procedures for treating conditions such as hallux valgus, etc. In this and other embodiments described herein, the anchoring systems and methods may be applicable to other bones than those specified with respect to that particular embodiment. For example, the systems and methods described with respect to FIG. 9 may be applicable to a connection to a proximal phalanx. For example, an additional ring shaped anchor (having the structure of primary anchor 830) may be attached to the second proximal phalanx, and connected to primary anchor 830 on the second metatarsal with a connector (e.g., a suture or biomaterial).

For example, an anchoring system as shown in FIG. 9 may be employed for fixating the relative position of the first metatarsal 810 to the second metatarsal 820 and thereby reducing the IM angle of the first metatarsal. In embodiments, the connector component 840 and secondary anchor 910 may provide for variable positioning and securing of the secondary anchor along the axial length of the connector component via a one-way ratcheting locking mechanism, a threaded engagement mechanism, and the like. For example, the outer surface of connector component 840 may have a plurality of spaced protrusions such as angular teeth, ridges, barbs, detents, ribs, threads, or the like, which are adapted to be retained in a mating surface provided on the inside surface of the secondary anchor 910. An example of such a configuration is shown in FIG. 9.

As shown in FIG. 9, secondary anchor 910 may include a female threaded portion 930 that engages with a male threaded portion 846 of connector component 840. By rotating, for example, connector component 840, a desired spacing between the first metatarsal 810 and the tension. The ratcheting may be automatic or may be actuated by the user. The ratcheting may be permanent or allow for future adjustment. Thus, the locking device may take the form of a releasable, two-way ratcheting device using a mechanism known in the art. Regardless, the invention should not be construed to be limited to any particular locking or ratcheting mechanism, as these types of mechanisms are well known in the art and can be readily made by techniques known to those of ordinary skill in the art. second metatarsal 820 may be achieved. In order to place the structure shown in FIG. 9, a coaxial hole may be placed, for example, in the first and second metatarsals. A smaller diameter hole that starts at the medial side of the first metatarsal 810 may be placed, extending through the second metatarsal 820. The hole may then be enlarged in the first metatarsal 810 to accommodate the larger diameter portion of the secondary anchor 910. Before, or after, these holes are drilled, a primary anchor 830 may be placed at least partially around the second metatarsal 820 and tissue (not shown) lying alongside the bone. The connector component 840 may then be slid into place, and a small incision used to provide access to add, for example, a retention clip 844 on the outside of the second metatarsal 820. The secondary anchor 910 may then be inserted into the larger hole in the first metatarsal 810 engaging the connector component 840. the connector component 840 and secondary anchor 910 may be utilized to reduce the first metatarsal 810 to the desired location.

The combination of mating connectors may function to resist motion of the connector component 840 in at least one direction. As shown in FIG. 9, the mating connections may also include securing mechanisms, such as clips 844, to secure the connector component 840 in place with respect to the primary anchor 830. In addition, the arrangement of the anchors may be reversed or modified so that the ring-shaped anchor 830 is placed around the first metatarsal and the anchor 910 is placed through the second metatarsal, or both metatarsals have ring-shaped anchors.

The connector component 840 may include features for securing the connector component to an outer surface of the anchor 830, such as holes, detents, grooves, rings, and the like. For example, as shown in FIG. 9, annular channels may be provided around the distal end 842 of the connector component 840 and one or more channels may be included at other appropriate locations. For example, depending on an expected bone width, one or more annular channels may be included in the vicinity of clip 844 between the first and second metatarsal to secure the connector component to the outer surface of anchor 830 on each side of the second metatarsal 820.

As shown in FIG. 9, the secondary anchor 910 may be adapted to have a slideable fit within the first metatarsal 810 and/or has an outer dimension that the allows the secondary anchor to act as a bushing to take up the space drilled in the first metatarsal or other bone. For example, secondary anchor 910 may have a smooth outer surface like a washer or a bushing having dimensions selected to slide within the hole drilled in the first metatarsal 810. The secondary anchor 910 has a flange 920, which abuts the proximal side of the first metatarsal 810 thereby restraining the first metatarsal between the secondary anchor 910 and the primary anchor 830 fixed to the second metatarsal 820.

Alternatively, primary anchor 830 and/or secondary anchor 910 may be connected a linkage to allow for a greater range of motion of the anchoring system, such as a ball joint and/or formed from a somewhat flexible material. In other words, if the axial motion of the anchoring system is along the y-axis of connector component 840, the linkage would permit motion along the x- or z-axis or a combination of x- and z-axes. For example, a ball joint or another type of lost-motion connection may be used to connect the primary anchor 830 and the connector component 840 and/or the connector component and the secondary anchor. This may enable the relative position of the metatarsal to be adjusted in all three dimensions.

Figure 10:
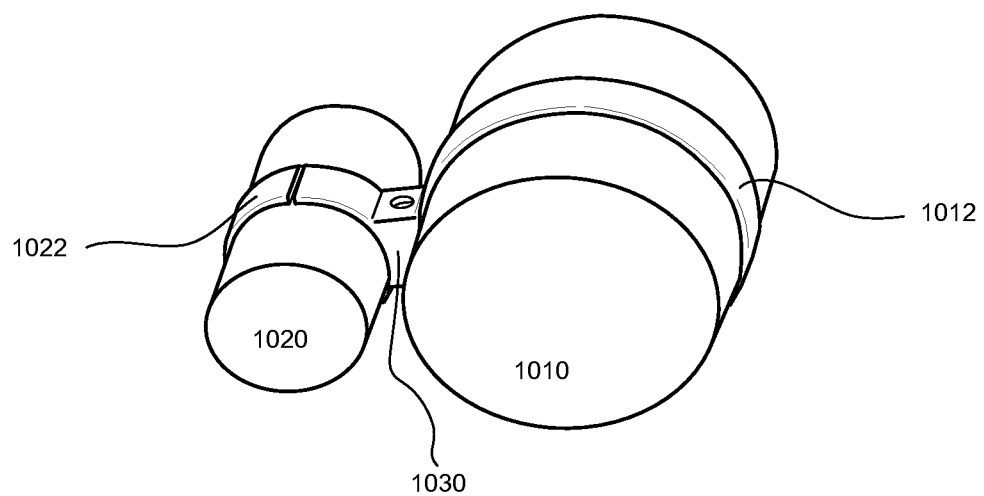
FIG. 10 is a schematic showing one embodiment of an anchoring system of the invention in which two ring-shaped anchors are disposed around the outsides of adjacent bones and separated by a spacer.

An alternative embodiment is depicted in FIG. 10, in which a first bone 1010 may be securely attached to a second bone 1020 via a primary anchor 1012 and secondary anchor 1022 with an appropriately sized spacer/connector 1030 in between. Thus, embodiments may also include anchors wrapping at least partially around two adjacent bones. For example, a primary anchor 1012 and a secondary anchor 1022 may be constructed according to design principles and materials as described further herein, and wrapped at least partially around a first metatarsal and a second metatarsal, respectively. A connector component 1030 may be included to secure the anchors to one another, such as by a fixed structure as shown in FIG. 10, or other connector configurations as described herein. In embodiments, a spacer component may be used as part of a connector component 1030 to achieve a desired separation distance between the bones. The spacer may be rigid or flexible, as needed, to accommodate a patient's prospective range of motion. Either of primary anchor 1012 and/or secondary anchor 1022 may be wrapped and/or compressed around the respective bone and associated tissue in order to apply pressure between the bone and the associated tissue. Additional anchors are also possible, such as connecting three or more anchors across the phalanges, metatarsals, or similar structures.

According to further aspects of the invention, surgical methods for reconstructing a joint may include entering the tissue of the joint by performing an incision, and placing a surgical anchor, such as primary anchor 740, around a first bone associated with the joint and at least partially around a tissue, such as a ligament, plantar plate, and the like, lying alongside the first bone. In embodiments, the tissue associated with the joint may be compressed to the first bone via the surgical anchor. After the joint is secured, including applying optional additional sutures, treatments, and the like, the incision may be closed.

In exemplary methods, compressing the primary anchor around the first bone and the tissue may include mechanical deformation of the primary anchor from a first state, in which the primary anchor is in an open shape, to a second state, in which the primary anchor is in a substantially closed ring shape, such as in FIGS. 4A and 4B. Embodiments may also include fixing the primary anchor in the substantially closed ring shape, for example, by securing the ends of the opening to one another, and or applying additional material around the outer circumference of the primary anchor.

In alternative embodiments, compressing the primary anchor around the first bone and the tissue may include compressing the primary anchor from a first closed state, in which the primary anchor has a first inner circumference, to a second closed state, in which the primary anchor has a second inner circumference that is smaller than the first inner circumference, such as in FIGS. 5A and 5B.

Figure 11:
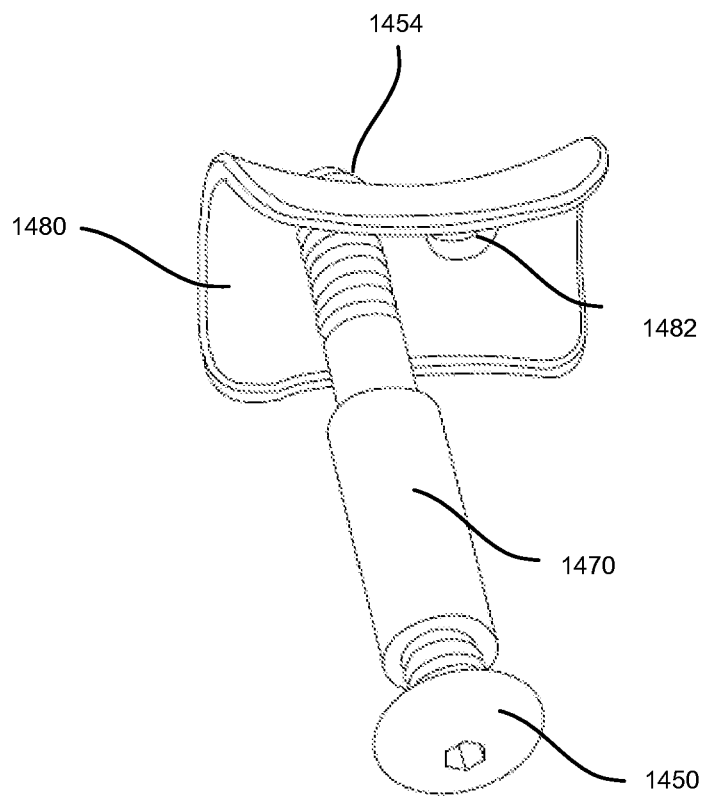
FIG. 11 is a schematic showing another embodiment of an anchoring system of the invention including an anchor that is contoured to fit around a metatarsal, and a connector that is secured to the anchor by a threaded engagement.

FIGS. 11-14 illustrate yet another embodiment of the invention including a threaded connector and a partial wrap-around anchor, which may take the form of a saddle. As shown in FIG. 11, anchor 1480 wraps partially around one of the bones being treated, e.g. a first or second metatarsal. Anchor 1480 may include one or more partial cavities or through-holes, such as through-holes 1482, for receiving an end of a connector, such as connector 1450, or the like. Through-holes, such as through-holes 1482, may include female threads, or other engagement means, to fixedly or adjustably secure the connector 1450 to the anchor 1480. However, in some embodiments, holes in the anchor 1480 may be relatively smooth, and not include engagement means. For example, connectors, such as connector 1450, may be prevented from passing through anchor 1480 by a flange included at the end of the connector, a detent and clip configuration, etc. In such cases, adjustment of a spacing between the bones may be provided by screwing the connector 1450 into the barrel 1470, or other adjustment means, thereby pulling the bones together.

As with other connectors described herein, connector 1450 may pass through a second bone (not shown), and optionally through a through-bone, wrap-around, or partial wrap-around anchor attached to the second bone. For example, barrel 1470, which may be configured as a through-bone anchor or adjustment mechanism, may be disposed in a tunnel drilled through the second bone, and may include threads, or other engagement means, to fixedly or adjustably secure the connector 1450 to the barrel 1470. It should be noted that, when used as a throughbone anchor, barrel 1470 may optionally include various combinations of the features described herein for securing the barrel as an anchor in the second bone. Connector 1450 may also include other adjusting mechanisms, such as multiple threaded segments that adjust with respect to each other when rotation of one segment is inhibited or prevented. For example, the connector 1450 may include two or more physically separated pieces with male threaded segments, and barrel 1470 may include internal female threads that engage with the male threads of at least one of the separate connector segments. The barrel 1470 may optionally be fixed to, or integrally formed with, one of the connector segments, or may include threaded engagements at both ends. Thus, the length of the overall connector 1450 may be expanded, or reduced, when rotation of the threaded end 1454 is inhibited or prevented by at least one male threaded segment moving with respect to the female threaded barrel 1470. The above adjustment mechanisms and threaded arrangements are merely exemplary, and various configurations falling within the scope of the invention will be appreciated by those of skill in the art upon understanding the concepts described herein.

Although FIG. 11 shows a single anchor 1480 as might be disposed on a first bone, it should be appreciated that a similar anchor may be included on an opposite bone to be treated. For example, the connector 1450 may pass through and abut one partial wrap-around anchor on the first metatarsal, pass through the first metatarsal, pass through the second metatarsal, and pass through and engage with another partial wrap-around anchor on the opposite side of the second metatarsal.

Figure 12:
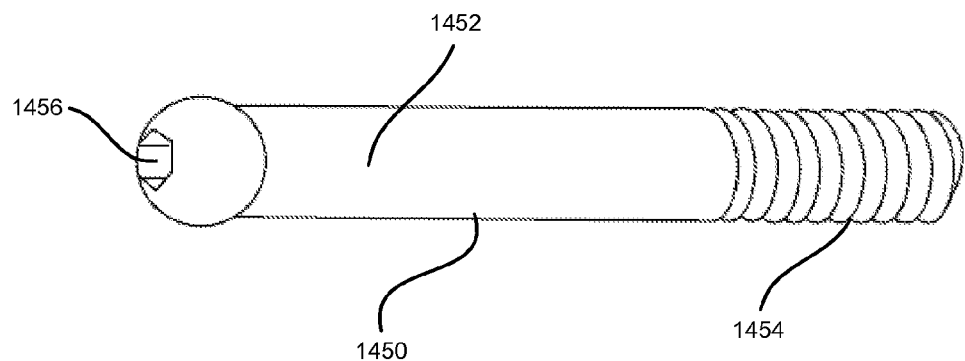
FIG. 12 is a schematic showing another embodiment of a connector having screw threads as a securing mechanism for primary or secondary anchors, and for positioning the anchors relative to each other.

As shown in FIG. 12, connector 1450 may include a shaft 1452 with threads 1454 at one end, and socket 1456, or other adjustment means, at the other end. Connector 1450 may be constructed of various materials, and combinations of materials, as described herein, such as elastic, inelastic, bioabsorbable and non-bioabsorbable materials, and combinations thereof. Threads 1454 may be configured to engage with various implantable, through-bone, wraparound, or partial wrap-around anchors described herein. Threads 1454 may be used as an adjustment mechanism to adjust a distance between first and second bones, e.g. by turning the shaft 1452 via socket 1456. In embodiments, connector 1450 may include threaded portions or other engagement and/or adjustment means described herein (e.g. angular teeth, ridges, barbs, detents, ribs, or the like) at both ends, or along the entire length, of the connector. Threads, or other engagement and/or adjustment means, at ends, or along the length, of the connector may be used to fixedly or adjustably secure the connector to opposing anchors, and/or spacers between the bones being treated. In the embodiment shown in FIG. 15, the end of the connector including socket 456 includes an enlarged flange, that may act as an anchor to prevent the connector 1450 from passing through one of the bones being treated, or passing through a wraparound or partial wrap-around anchor. Additional details of exemplary partial wrap-around anchor 1480 are shown in FIGS. 13 and 14.

As described further below, anchor 1480 may be configured to fit closely with a particular bone, such as a first or second metatarsal, and associated tissue. In embodiments, either, or both, of a primary anchor and a secondary anchor such as anchor 1480, may be contoured to an anatomical shape of a bone to be treated, e.g. a metatarsal, phalanx, etc. Such contours may include developable and/or non-developable surfaces. Developable surfaces may include, for example, cylindrical or conical shapes, whereas non-developable surfaces include Gaussian curvature, e.g. partial spheroids, three-dimensional saddles, depressions, etc. In embodiments, a preformed contour of at least one of the primary anchor and the secondary anchor may include a saddle, or depression, that substantially matches an anatomical shape of the bone to be treated, e.g. a metatarsal (such as shown in FIG. 1), or phalanx. FIGS. 13 and 14 show three-dimensional saddle form of anchor 1480 in more detail. Saddle 1484 includes both a cylindrical curvature around the bone to be treated and a depression around the circumference of the bone, which may be preferable for fitting around a metatarsal such as shown in FIG. 1. Such three-dimensional curves may be beneficial in closely fitting the anchor to the bone and associated tissue, and evenly distributing forces across the bone surface, as well as helping to prevent axial displacement of the anchor and/or tissue after being secured to the bone.

Figure 13:
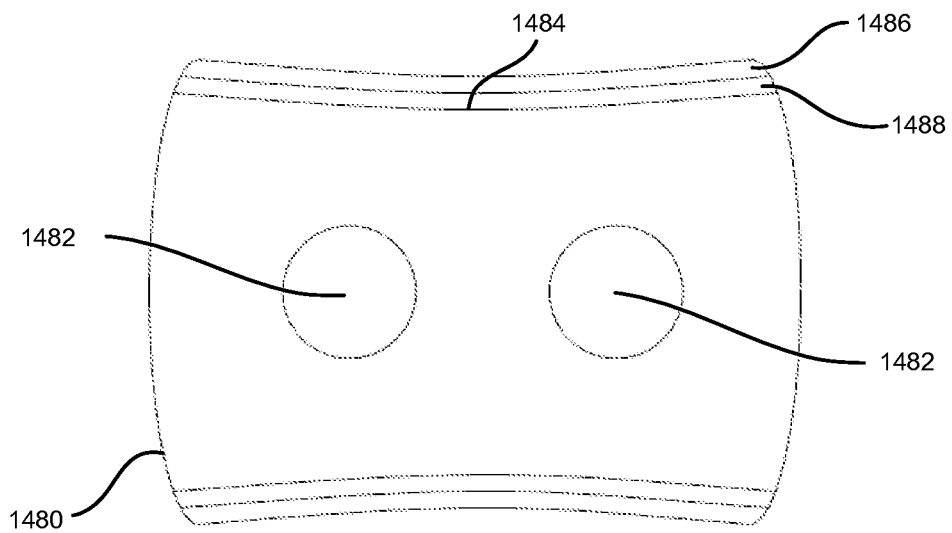
FIGS. 13 and 14 are schematic side and front elevation views showing further details of the anchor shown in FIG. 11, including dorsal and plantar extension.
Figure 14:
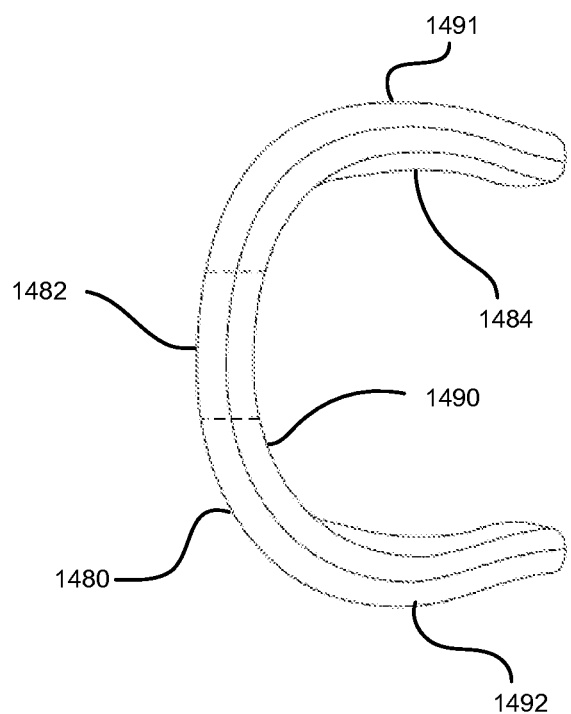

As shown in FIG. 13, the wall of the anchor 1480 may include a plurality of (in this case two) cavities or through-holes 1482 to receive and/or engage with the connector(s). Thus, according to embodiments, either, or both, of the primary anchor and the secondary anchor may be adapted to be secured to a plurality of connectors, e.g. secured to two connectors disposed diagonally, crossing or parallel to one another. In embodiments, one or more partial cavities (i.e. cavities that do not form through-holes), or perforations such as through-holes 1482, of the primary and/or secondary anchor(s), may be threaded for fixedly, or adjustably, securing the connector(s) to the primary or secondary anchor. By way of further example, if partial cavities are used, instead of through-holes, the connector may be securely seated in the anchor by bottoming out a fastener, such as a bolt, in the partial cavity. In such cases, adjustment of a distance between bones may be achieved by adjusting the relative distance of the other anchor, e.g. by screwing the connector 1450 into barrel 1470, by a ratcheted connector end, etc.

As also shown in FIG. 13, anchor 1480 may be constructed from layers 1486, 1488 of different material, depending on intended usage. For example, a first layer 1486 may be comprised of a relatively rigid material that is effective for distributing the tensile force from the connector across a surface of the bone, and also for assuming and/or maintaining a desired shape, e.g. an anatomical shape of the bone to be treated. Such materials may be, for example, thermosetting or thermoplastic polymers or other materials. A second layer 1488 may be comprised of a material that is particularly suited for contact with the bone to be treated and/or tissue to be secured, and may include, for example, substances such as those described herein intended to promote (or retard) bone growth or adhesion may be used in layer 1488 depending on whether the anchor 1480 is intended to be left in place, bioabsorbed or removed.

As shown in FIG. 14, anchor 1480 may have a base portion 1490 configured to extend axially along a length of the bone, and one or more flanges, such as dorsal and plantar extensions 1491, 1492, attached to the base portion 1490. Flanges, such as dorsal extension 1491 and/or plantar extension 1492, may extend generally transversally from base portion 1490, or at other angles depending on intended usage, and may be adjustable, such as by using a deformable material, hinges, etc. Dorsal and plantar extensions 1491, 1492 may be configured to wrap partially around the bone and/or associated tissue. Such extensions may be used, for example, to provide additional security to the bone fixation, and may also be used to hold tissue, such as the plantar plate, in position after reconstruction and/or repair of an affected joint. The surface of layer 1488, preferably in the plantar extension 1492, may be treated, or otherwise configured, to more securely hold associated tissue, such as by providing a relatively rough or tacky surface.

In embodiments, the disclosed surgical anchoring system may be employed for surgical repair of the MTP joint including fixation of the native PP at the phalanx, and other realignment such as the lumbrical and interosseous tendons. In embodiments, it is possible that other soft tissues could be incorporated in the reconstruction, e.g. lumbricals and interosseous, as well as the collateral ligaments.

Figure 15:
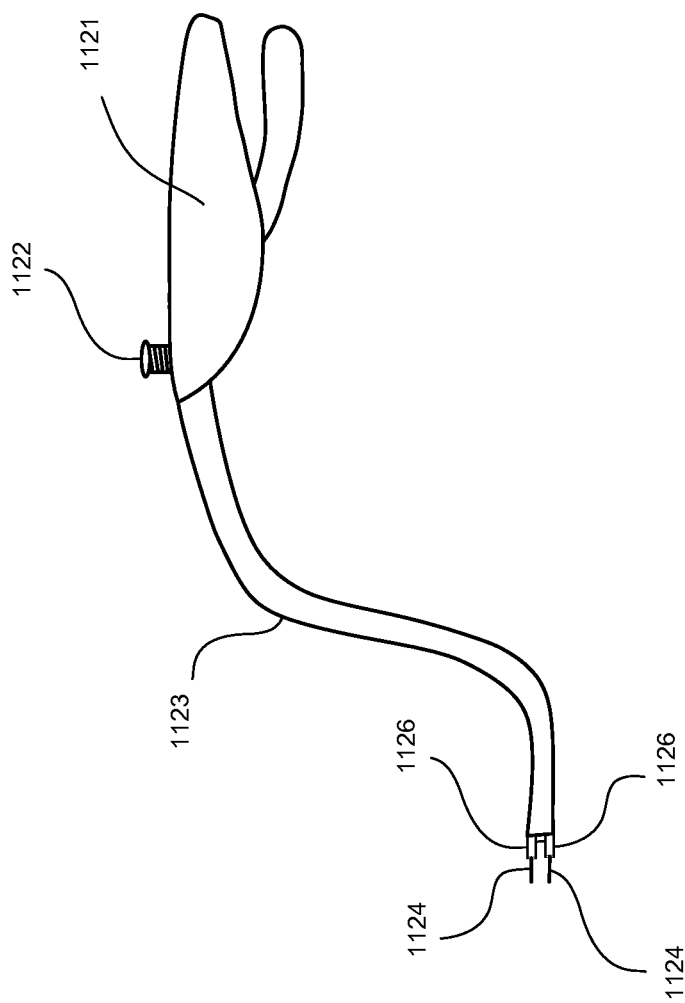
FIGS. 15-21 are simplified side views showing details of an exemplary joint repair procedure using an anchor and a positioning device according to yet further aspects of the invention.

FIGS. 15-21 are simplified side views showing details of an exemplary joint repair procedure using an anchor and a positioning device according to yet further aspects of the invention. As shown in FIG. 15, a positioning device 1121 may include an adjustment mechanism 1122, an arm 1123, and extendable and/or retractable elongate members 1124 for positioning and securing tissue to a fixation device. The members 1124 may be supported for axial movement along the length of arm 1123 by any means known in the art, e.g. individual tubes supported by arm 1123. For example, each of members 1124 may be surrounded by an individual sheath 1126, e.g. to provide additional rigidity, axial support, etc. as needed.

Figure 16:
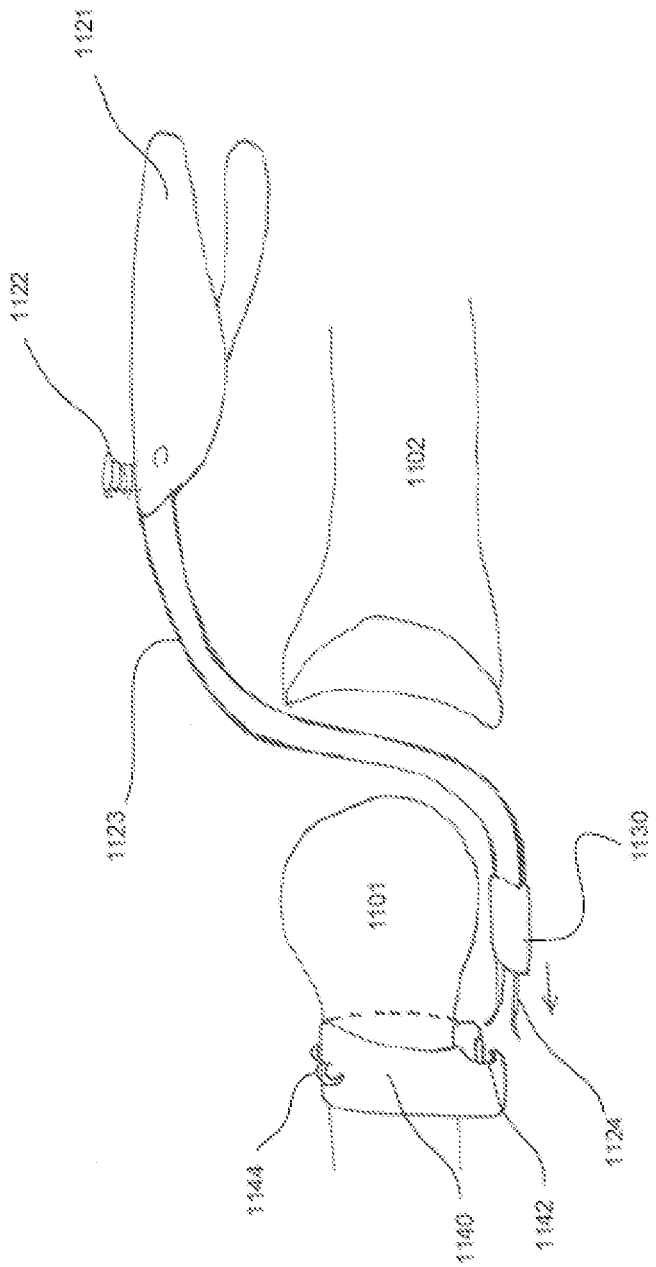

Members 1124 may be made from various materials or combinations of materials and may include different material segments along the length of the member. In operation, the members 1124 may be sized and configured, for example, to puncture a tissue and assist in securing the tissue to a bone alongside the tissue. In embodiments, and as shown in FIG. 16, the members 1124 may be forced through spaced portions of plantar plate 1130, which has become detached or partially detached from its metatarsal 1101. Members 1124 may include barbs, or other means for securing a portion of the members 1124 to the penetrated tissue.

The arm 1123 may be, for example, a rigid or flexible material and may be cannulated for allowing the members 1124 to connect to the adjustment mechanism 1122. The adjustment mechanism 1122 may comprise any means known in the art to extend and/or retract the members 1124. For example, mechanism 1122 may wind and unwind the members 1124 to extend and retract them from the arm 1123, as described further below. The arm 1123 may be shaped and/or or sufficiently flexible and/or adjustable to fit between the joint of two bones, such as metatarsal 1101 and proximal phalanx 1102 shown in FIG. 16. Exemplary methods may include a topside approach, such as shown in FIG. 16, where the positioning device 1121 is inserted from an incision that is opposite the tissue to be reattached. Alternative embodiments may include approaching the joint from an incision that is on the same side as the tissue to be reattached, or other approaches depending on, for example, the joint and surrounding physiology.

As further shown in FIG. 16, a fixation device may take the form of a ring-shaped anchor 1140 and may include one or more attachment points 1144, as well as an independent interior contour 1142 for receiving the tissue to be secured. For example, the anchor 1140 may have a first contour for closely accommodating the metatarsal 1101 or other bone, and a second contour, that is non-continuous with, and/or different than, the first contour. The inner surface in the vicinity of the contour 1142 may also include features for axially securing the tissue in the anchor, such as, for example, surface treatments, ridges, barbs, etc.

Figure 17:
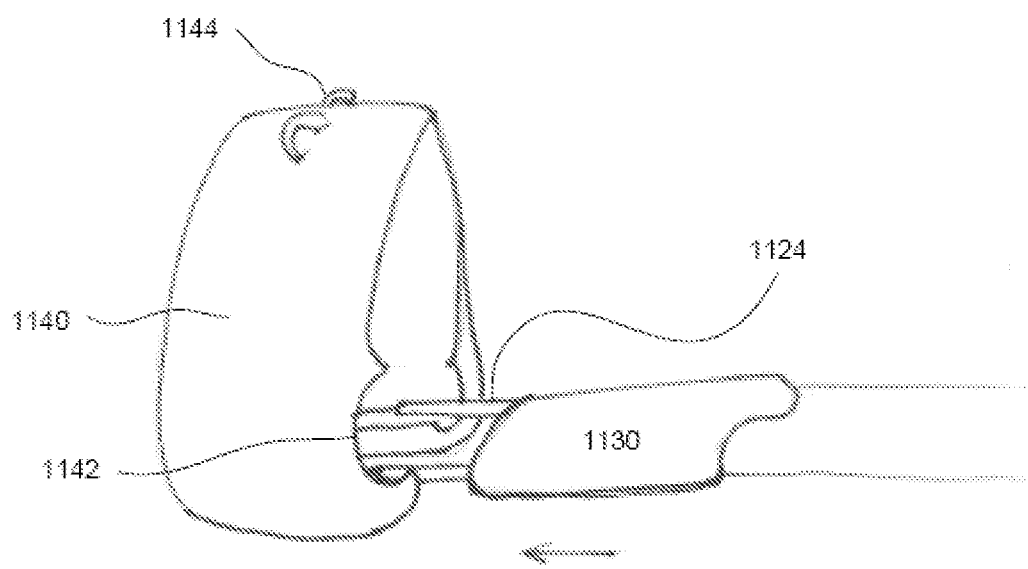

As shown in FIG. 17, the arm 1123 of positioning device 1121 may pressed against a detached or partially detached tissue, such as plantar plate 1130, to adjust a position of the tissue with respect to a fixation device, such as anchor 1140. For example, the positioning device 1121 may be used to push and/or pull the tissue at least partially within a pre-positioned anchor. In embodiments, a fixation device, such as anchor 1140, may be initially secured to the bone, e.g. by suturing, compression, etc., prior to inserting the tissue in a receiving portion of the fixation device. In other embodiments, the fixation device may be held in place by any other means known in the art while the tissue is inserted in the receiving portion, or the tissue may be placed in a desired location against the bone prior to positioning the fixation device.

Figure 18:
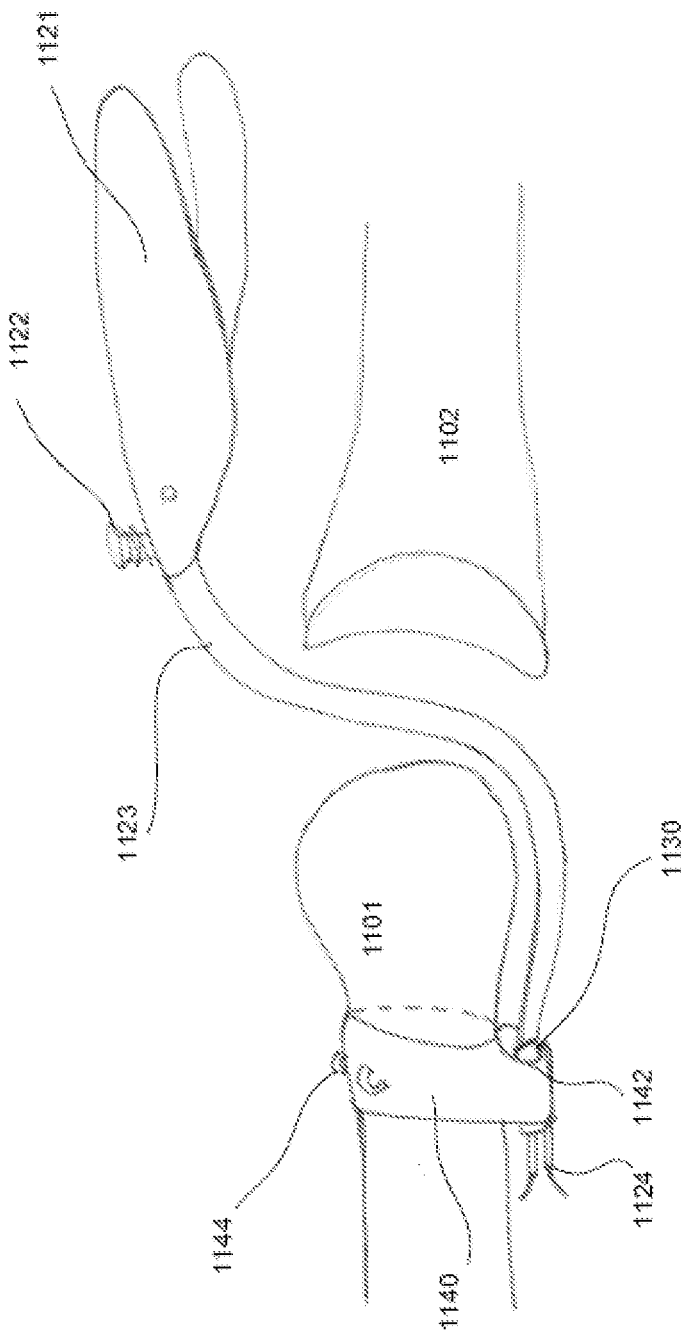

As shown in FIG. 18, the plantar plate 1130 may be positioned in the anchor 1140, and the anchor 1140 may be secured to the bone 1101, such as by compressing the anchor around the bone, such that the plantar plate 1130 is pressed against the bone 1101.

Figure 19:
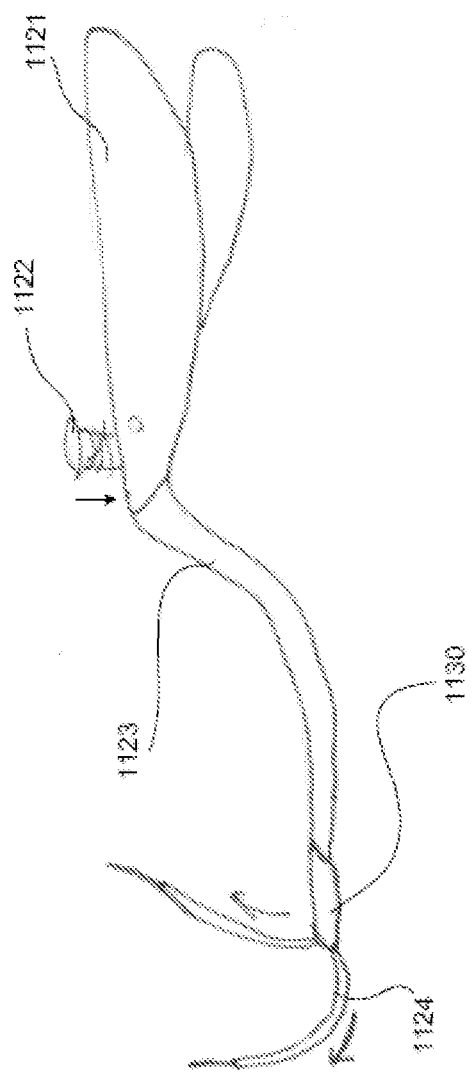

As shown in FIG. 19, the member 1124, and/or sleeves 1126, or portions thereof, may be extended from the positioning device 1121, e.g. by rotating adjustment mechanism 1122, and/or by pulling on free ends of the members. In embodiments, the free ends of the members may be approached from above and pulled toward the upper side of the bone. This may be done, for example, after the anchor 1140 is secured to the bone 1101, thereby holding the plantar plate 1130 in place.

Figure 20:
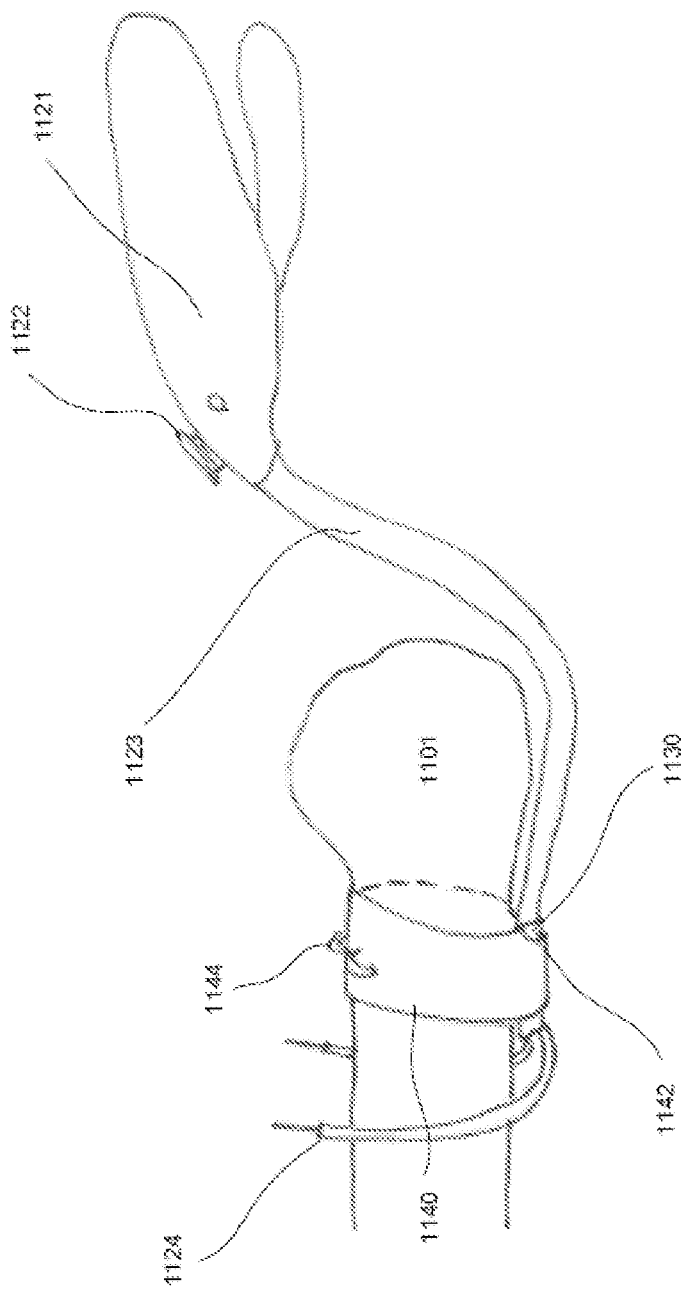

The free ends of the members 1124 may be pulled and/or fed toward the upper side of bone 1101, as shown in FIG. 20. The members 1124 may be configured such that, when fully extended, barbs or other securing means engage the plantar plate 1130 and facilitate the members holding the tissue in position. Alternatively, the members 1124 may form a "Y"

shape, with the free ends at the top of the "Y". At full extension, the tissue may be secured at the cradle of the "Y" and the positioning device 1121 may be configured to cut, or otherwise separate, the bottom of the "Y" from the free ends.

Figure 21:
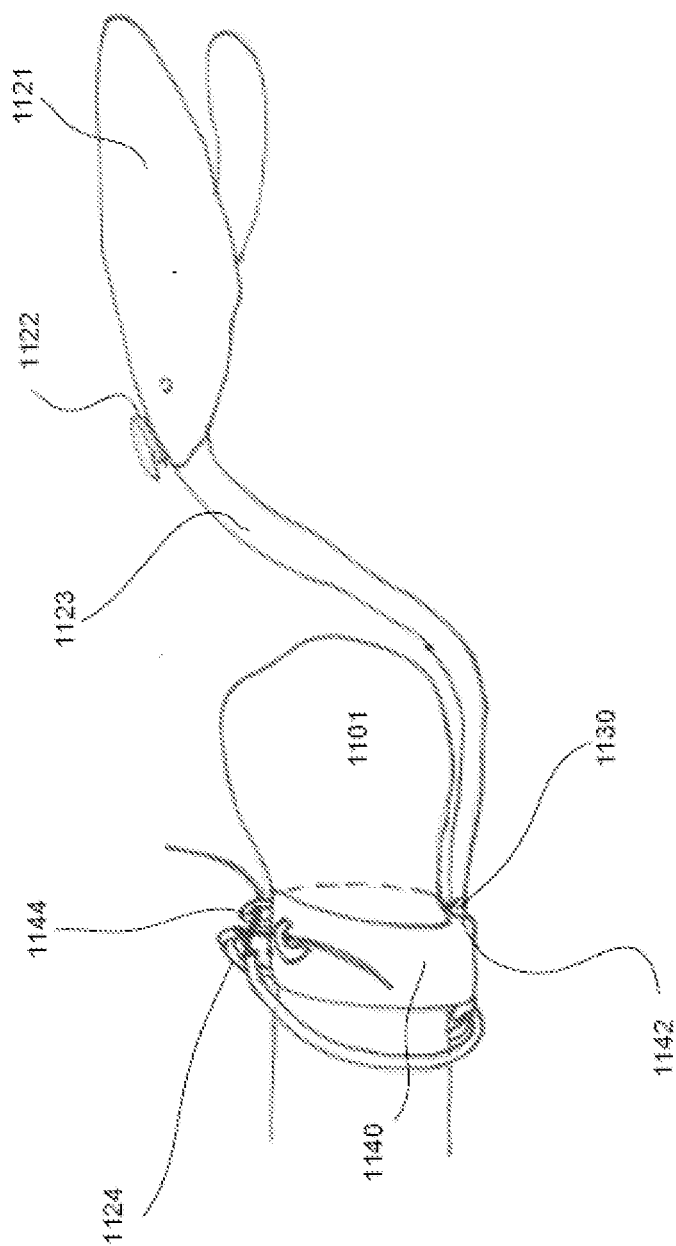

As shown in FIG. 21, free ends of the members 1124 may be secured on the upper side of the bone 1101 and may be secured to the anchor 1140 through attachment points 1144, thereby fixing the plantar plate to the bone 1101. Once the elongate members 1124 are secured to the anchor 1140, the positioning device 1121 may be separated and removed. Like anchor 1140, the members 1124 may be biodegradable or removable.

According to another feature of some embodiments, bony healing may be induced during the surgical procedures by introducing bone growth factors such as bone morphogenetic proteins (BMPs) and basic fibroblast growth factor (bFGF) to the target area undergoing correction. These two classes of bone growth factors have been shown to accelerate bone regeneration, bone healing to prosthetic-like implants, and increase strength and stability to the bony callus. The bone growth factors could be delivered to the target area by a variety of methods. One method may be to introduce the bone growth factors in combination with a collagen matrix, which could be a gel- or sponge-like material, to the target area. The bone growth factor may then stimulate the patient's own bone cells into action, while the collagen may provide the scaffolding into which the stimulated bone cells can grow. In the end, bone could replace the collagen scaffold, which may be eventually resorbed.

Another method of delivery may be to coat the anchors and/or connector components with the bone growth factor in combination with hydroxyapatite, which may have a synergic stimulative effect on the bone cells. For this to be accomplished, an effective amount of the bone growth factor would be absorbed to a gritblasted hydroxyapatite coated anchor or screw prior to implantation into the bone.

However, an alternate method to the delivery of recombinant bone growth factors may be through gene therapy. Delivery by gene therapy may be more cost effective because ex vivo production of DNA for clinical use is inexpensive compared with traditional methods of protein production. Also, gene therapy may be a more efficient way to deliver the bone growth factors compared with traditional protein delivery. One desirable way to utilize gene therapy in the surgical procedure may be to introduce plasmid-encoded proteins capable of inducing bone growth to the area of distraction. This may be accomplished by introducing biodegradable matrices, such as collagen sponges, containing expression plasmid DNA encoding bone growth factors, also known as gene-activated matrices (GAMs), to the target area.

The description and examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the medical sciences, orthopedic surgery, or related fields are intended to be within the scope of the appended claims.

The disclosures of all references and publications cited above are expressly incorporated by reference in their entireties to the same extent as if each were incorporated by reference individually.

The invention claimed is:

1. A surgical method for repairing and/or reconstructing an MTP joint of a foot affected with hallux valgus, said method comprising the steps of:
    making one or more incisions to the foot;
    attaching a first anchor to a first metatarsal bone of the foot through the one or more incisions;
    attaching a second anchor to a second metatarsal bone of the foot through the one or more incisions;
    providing a connection with a connector between and secured to the first anchor and the second anchor; and
    adjusting a distance between the first metatarsal bone and the second metatarsal bone by adjusting and fixing a length of the connector between and secured to the first anchor and the second anchor;
    wherein the attaching of one of the first anchor and the second anchor comprises placing one of the first and the second anchors around or through the corresponding first metatarsal bone or the second metatarsal bone and the other one of the first anchor and the second anchor comprises a clamping anchor, and the attaching of the other one of the first and the second anchors comprises placing the clamping anchor around the first metatarsal or second metatarsal that corresponds to the clamping anchor to clamp a plantar plate tissue of the foot within the clamping anchor between the clamping anchor and the first metatarsal bone or the second metatarsal bone that corresponds to the clamping anchor to adjust the MTP joint.

2. The method of claim 1, wherein placing the clamping anchor around the first metatarsal or second metatarsal comprises compressing the clamping anchor around the first metatarsal or second metatarsal and the tissue alongside the first metatarsal or second metatarsal that corresponds to the clamping anchor.

3. The method of claim 2, wherein said step of compressing the clamping anchor includes closing the clamping anchor from a first state, in which the clamping anchor is in an open shape, to a second state, in which the clamping anchor is in a substantially closed ring shape.

4. The method of claim 2, wherein said step of compressing the clamping anchor includes compressing the clamping anchor from a first closed state, in which the clamping anchor has a first inner circumference, to a second closed state, in which the clamping anchor has a second inner circumference that is smaller than the first inner circumference.

5. The method of claim 1, further comprising the steps of: creating a bore across the first metatarsal; and inserting the connector through the bore.

6. The method of claim 5, wherein said step of providing a connection comprises preventing the connector from pulling back through the second anchor.

7. The method of claim 5, wherein said step of adjusting a distance comprises adjustably engaging a portion of the connector with one of the first anchor and the second anchor.

8. The method of claim 5, wherein said step of providing a connection comprises adjustably engaging a threaded portion of the connector with a threaded surface of one of the first anchor and the second anchor.

9. The method of claim 1, wherein said first anchor is placed around the first metatarsal bone to clamp the plantar plate tissue within the first anchor between the first anchor and the first metatarsal bone and said and said second anchor is placed around the second metatarsal bone to clamp the plantar plate tissue with the second anchor between the second anchor and the second metatarsal bone.

10. The method of claim 1, further comprising: penetrating the tissue alongside the first metatarsal bone with an elongated member;
adjusting a position of the tissue alongside the first metatarsal bone such that the plantar plate tissue is at least partially within the first anchor; and
fixing the plantar plate tissue to the first anchor with the elongated member.

11. The method of claim 10, further comprising feeding the elongated member through a positioning device and adjusting the position of the tissue with the positioning device.

12. The method of claim 1, wherein the clamping anchor is the first anchor.

13. The method of claim 1, wherein clamping the tissue comprises clamping a plantar plate to at least one of the first metatarsal and the second metatarsal.

14. The method of claim 13, wherein at least one of the first and second anchors is formed as a full or partial ring.

15. The method of claim 14, further comprising attaching a third anchor to a proximal phalanx of the foot.

16. A surgical method for repairing and/or reconstructing an MTP joint of a foot affected with hallux valgus, said method comprising the steps of:
providing a surgical kit comprising a first anchor configured to connect to a first metatarsal bone through one or more incisions to the foot, a second anchor configured to connect to a second metatarsal bone through the one or more incisions, and a connector configured to provide a connection between and secured to the first anchor to the second anchor, wherein the length of the connector between the first and second anchor is adjustable and fixable so that a distance between the first metatarsal bone and the second metatarsal bone is adjusted;
treating the hallux valgus condition of the foot by clamping a plantar plate tissue of the foot with one of the first and second anchors to one of the first and second metatarsal bones of the foot by placing the one of the first and second anchors through the one or more incisions to the foot, around the one of the first and second metatarsal bones and around the corresponding plantar plate tissue to adjust the MTP joint;
wherein the other of the first and second anchors is configured to be placed through the one or more incisions to the foot, around or through the other one of the first and second metatarsal bones; and
wherein the connector is configured to adjust the distance between the first metatarsal bone and the second metatarsal bone by adjusting and fixing the length of the connector between and secured to the first anchor and the second anchor.

17. The method of claim 16, comprising adjusting an intermetatarsal angle between the first metatarsal and the second metatarsal.

18. The method of claim 17, comprising attaching the first anchor to the first metatarsal and attaching the second anchor to the second metatarsal.

19. The method of claim 18, comprising adjusting a distance between the first metatarsal and the second metatarsal by adjusting a relative position of the connector and at least one of the first anchor and the second anchor.

20. The method of claim 16, comprising providing the surgical kit with a third anchor configured to connect to at least one of a first proximal phalanx and a second proximal phalanx.

21. The method of claim 19, comprising attaching the third anchor to one of the first proximal phalanx of the foot or the second proximal phalanx of the foot.

* * * * *